United States Patent
Boretto et al.

(10) Patent No.: US 6,941,750 B2
(45) Date of Patent: Sep. 13, 2005

(54) METHOD OF DETERMINING THE AMOUNT OF PARTICULATE ACCUMULATED IN A PARTICULATE FILTER

(75) Inventors: Gianmarco Boretto, Nichelino (IT); Silvio Corrias, Orbassano (IT)

(73) Assignee: C.R.F Societa Consortile per Azioni, Orbassano (IT)

( * ) Notice: Subject to any disclaimer, the term of this patent is extended or adjusted under 35 U.S.C. 154(b) by 77 days.

(21) Appl. No.: 10/350,365

(22) Filed: Jan. 24, 2003

(65) Prior Publication Data
US 2003/0167757 A1 Sep. 11, 2003

(30) Foreign Application Priority Data
Jan. 25, 2002 (IT) .................................... TO2002A0072

(51) Int. Cl.$^7$ ................................................ F01N 3/00
(52) U.S. Cl. ........................... 60/297; 60/274; 60/277; 60/311; 55/DIG. 30; 73/118.1
(58) Field of Search ...................... 60/274, 295, 297, 60/311, 276, 277; 55/DIG. 30, 523; 73/118.1, 23.31, 23.32

(56) References Cited

U.S. PATENT DOCUMENTS

| | | | | | |
|---|---|---|---|---|---|
| 4,390,355 A | * | 6/1983 | Hammond et al. | ............ | 55/523 |
| 4,404,795 A | * | 9/1983 | Oishi et al. | .................... | 60/274 |
| 4,643,749 A | * | 2/1987 | Miura | .......................... | 55/523 |
| 5,171,335 A | * | 12/1992 | Kojima et al. | ................ | 55/523 |
| 5,511,413 A | | 4/1996 | Pfister et al. | | |
| 2003/0172642 A1 | * | 9/2003 | Nakatani et al. | .............. | 60/277 |

FOREIGN PATENT DOCUMENTS

| | | | | |
|---|---|---|---|---|
| DE | 37 23 470 A1 | | 1/1989 | |
| DE | 10160944 A1 | * | 7/2003 | ........... F01N/11/00 |
| EP | 1 081 347 A1 | | 3/2001 | |
| EP | 1 108 866 A2 | | 6/2001 | |

* cited by examiner

*Primary Examiner*—Tu M. Nguyen
(74) *Attorney, Agent, or Firm*—Berenato, White & Stavish (57) ABSTRACT

A method of determining the amount of particulate accumulated in a particulate filter, is based on determining possible variations in the spatial distribution and/or physical-chemical properties of the particulate as a function of engine operating conditions and past particulate accumulation in the particulate filter. A number of reference values defining a relationship between the amount of particulate accumulated in the particulate filter and the pressure drop across the particulate filter are mapped, each of the reference values relating to a respective steady engine operating condition in which particulate is accumulated in the particulate filter. In a given engine operating condition, an operating value of the parameter is then determined as a function of the reference value of the parameter relative to the same steady engine operating condition, and of past particulate accumulation in the particulate filter.

12 Claims, 9 Drawing Sheets

METHOD OF DETERMINING THE AMOUNT OF PARTICULATE ACCUMULATED IN A PARTICULATE FILTER

The present invention relates to a method of determining the amount of particulate accumulated in a particulate filter.

The present invention may be used to advantage, though not exclusively, in automotive applications, and particularly in internal combustion engines, especially diesel engines, to which the following description refers purely by way of example.

The present invention, in fact, may also be used in other than automotive applications, as for filtering particulate emitted by any system equipped with particulate filters, such as fuel burners, etc.

BACKGROUND OF THE INVENTION

As is known, in many countries, the regulations governing atmospheric pollution are becoming increasingly strict with regard to the composition of internal combustion engine exhaust gas.

In the case of diesel engines in particular, the main problems are posed not so much by carbon monoxide (CO) and hydrocarbons (HC) as by nitric oxides (NOx) and particulate in the exhaust gas.

Various sources have shown that even modern direct-injection diesel engines introduced onto the market at the end of the 90s are characterized by serious particulate emissions.

Numerous methods have been proposed whereby to minimize the particulate content of exhaust gas emitted into the atmosphere. Of these, fitting the exhaust pipe with a particulate filter has long been acknowledged in engine technology as undoubtedly the final solution to the problem of diesel engine particulate emissions.

A particulate filter—also known as particulate trap (soot catcher or soot trap)—normally comprises a number of parallel, porous-walled, alternately obstructed channels.

More specifically, the obstructions force the exhaust gas to flow through the lateral walls of the channels, so that the unburned particles constituting the particulate are first retained in the pores of the lateral walls, and, when the pores eventually become clogged, accumulate and form a porous layer on the inner surfaces of the channel walls.

As the particulate accumulates on the inner surfaces of the channel walls, the pressure drop through the filter, and therefore the backpressure generated by the filter, also increases.

If not removed eventually, an excessive accumulation of particulate therefore results in:
- impaired performance, driving comfort, and consumption of the engine, until the engine eventually stalls; and
- destruction of the filter itself in the event of self-firing and uncontrolled combustion of the particulate. In particular driving conditions, a large accumulation of particulate may give rise to "critical" regeneration phenomena consisting in sudden, uncontrolled particulate combustion, thus resulting in overheating of the ceramic matrix of the filter and in possible damage to the filter itself.

The trapped particulate must therefore be removed regularly by regenerating the particulate filter, which, in engine technology, means burning the accumulated particulate (mainly composed of carbon, C) which, in contact with the oxygen in the exhaust gas, is converted into carbon monoxide CO and carbon dioxide $CO_2$.

This reaction, however, only occurs spontaneously (i.e. without using additives) at temperatures over roughly 600° C., which are much higher than those at the filter inlet in normal engine operating conditions.

In certain conditions, i.e. on detecting a given accumulation of particulate in the filter, the exhaust gas temperature at the filter inlet must therefore be increased artificially to initiate particulate combustion.

Numerous methods of artificially increasing exhaust gas temperature at the filter inlet to initiate particulate combustion have been proposed and/or actually implemented.

One of the main drawbacks of current on-vehicle particulate combustion initiation methods lies in regeneration of the particulate filter being initiated cyclically on the basis of mileage, e.g. every 500 or 1000 km, independently of the actual amount of particulate accumulated in the filter.

Mileage-based particulate filter regeneration has recently been proved beyond all doubt to be totally inefficient, by frequently initiating regeneration of the filter unnecessarily, or conversely, by not initiating regeneration of the filter even when actually required.

Tests have shown particulate accumulation in the filter does not depend solely on mileage, but is also fairly seriously affected by other factors, such as vehicle mission profile (e.g. urban or highway driving) and driving style (e.g. sport oriented). Moreover, any engine imperfections, which may result in a considerable increase in particulate emissions, are not taken into account; in which case, particulate may accumulate in the filter to the extent of seriously impairing engine and filter reliability.

To accurately determine the amount of particulate accumulated in the filter, so as to only initiate regeneration of the filter when the amount exceeds given levels, various authors have proposed numerous physical models by which to calculate the mass of accumulated particulate on the basis of exhaust gas flow and temperature and the pressure drop through the filter. All the models proposed are substantially based on the assumption that particulate distribution inside the filter channels and the physical-chemical properties of the particulate remain even and constant, independently of variations in the operating condition of the engine and in past particulate accumulation.

For example, in Konstandopoulos A. G., Kostoglou M., Skaperdas E., Papaioannou E., Zarvalis D., and Kladopoulou E., "Fundamental Studies of Diesel Particulate Filters: Transient Loading, Regeneration and Ageing", SAE 2000-01-1016, 2000, assuming even (axial and radial) spatial particulate distribution inside the channels, an analytical particulate filter model is proposed which takes into account various factors, such as filter geometry, physical characteristics of the filter material, particulate characteristics, etc., which are assumed constant, independently of variations in the operating condition of the engine and in past particulate accumulation.

For the sake of clarity, the following is the complete equation (eq. 1) developed by the Applicant from the considerations made in the above publication as a model of the particulate filter, possibly with a catalytic converter upstream from the filter:

$$\Delta P_{DPF}\left(\frac{\Delta P_{DPF}}{2} + P_{atm}\right) = \frac{\mu_o T^{\delta+1} R}{2 M_w} Q_m \frac{(H+w)^2}{V_{trap}} \cdot \quad \text{(eq. 1)}$$

$$\left[\frac{w}{k_m H} - \frac{1}{4k_s}\ln\left(1 - \frac{m_s}{\rho_s} \cdot \frac{1}{NLH^2}\right) + \right.$$

-continued $$\frac{4}{3}\frac{FL^2}{H^4} + \frac{4}{3}\frac{FL^2}{H^4}\left(1 - \frac{m_s}{\rho_s} \cdot \frac{1}{NLH^2}\right)^{-2}\right] +$$

$$\frac{TR}{M_w}Q_m^2 \frac{(H+w)^4}{H^2 V_{trap}^2}\left[\frac{w}{4k'_m} + 2\xi\left(\frac{L}{H}\right)^2\right] +$$

$$\frac{\mu_o T^{\delta+1} R}{2M_w} Q_m \frac{(H_{cat} + w_{cat})^2}{V_{cat}}\left[\frac{4}{3}\frac{FL_{cat}^2}{H_{cat}^4}\right]$$

where:

$V_{trap}$,H,L,N,w are the following geometric properties of the filter: volume, cell size, length, number of open cells, wall thickness;

$k_m$,$k'_m$ are the following properties of the filter material: linear and nonlinear permeability;

$V_{cat}$,$H_{cat}$,$L_{cat}$,$W_{cat}$ are the following geometric properties of the catalyst: volume, cell size, length, wall thickness;

R,F,ξ are the following constants: gas constant (8.314 J/(K·mol)), gas friction coefficient in square-section conduits (~28.454), inertial term (~3);

$P_{atm}$,$M_w$,T,$\mu_o$ are the following exhaust gas properties: absolute pressure downstream from the filter (may be considered roughly equal to atmospheric pressure), gas mean molecular weight, temperature, viscosity factor;

$m_s$,$k_s$,$\rho_s$ are the following physical-chemical particulate properties: mass, permeability, density; and $\Delta P_{DPF}$,$Q_m$ are the total pressure drop across the filter and mass exhaust gas flow.

Implementing the above equation at engine control unit level to determine the particulate mass $m_S$ accumulated in the filter would be particularly complex, in that defining and calculating the particulate mass $m_S$ as a function of the other variables involved would call for computing power far beyond that of currently used automotive engine control units.

Even if the equation could be implemented in the engine control unit, the results would be totally unsatisfactory. Bench and on-vehicle tests conducted by the Applicant, in fact, have shown that assuming even, constant particulate distribution in the filter channels and constant physical-chemical properties of the particulate, independently of variations in the operating condition of the engine and in past particulate accumulation, makes it impossible to obtain a correct estimate of the amount of particulate accumulated in the filter in real operating conditions. Which is why regeneration control systems based on measuring exhaust gas flow and temperature and the pressure drop across the filter have never be employed in the automotive industry.

SUMMARY OF THE INVENTION

It is an object of the present invention to provide a method of determining the amount of particulate accumulated in a particulate filter, designed to eliminate the aforementioned drawbacks, and which provides for regenerating the particulate filter when this contains a known quantity of particulate.

According to the present invention, there is provided a method of determining the amount of particulate accumulated in a particulate filter, as claimed in claim 1.

BRIEF DESCRIPTION OF THE DRAWINGS

A preferred, non-limiting embodiment of the present invention will be described by way of example with reference to the accompanying drawings, in which.

DETAILED DESCRIPTION OF THE INVENTION

Figure 1:
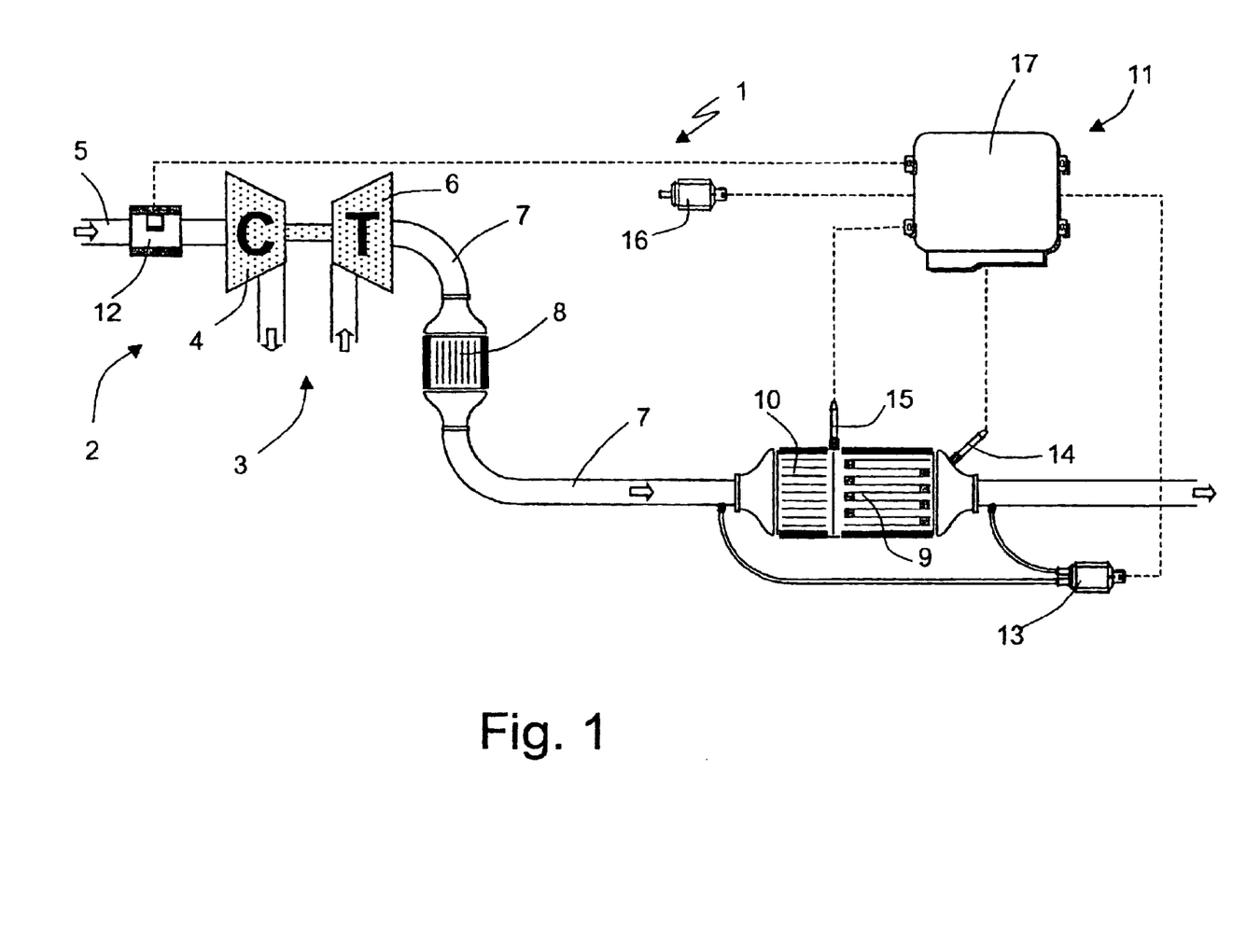
FIG. 1 shows, schematically, an exhaust system comprising a particulate filter and relative devices for measuring exhaust gas flow and temperature, and the pressure drop of the particulate filter.

Number 1 in FIG. 1 indicates as a whole an exhaust system of an engine 2, in particular a diesel engine. In the non-limiting example shown, diesel engine 2 in FIG. 1 is a turbocharged type, and comprises a turbocharger 3 defined by a compressor 4 located along an air intake conduit 5, and by a turbine 6 connected to compressor 4 and located along an exhaust conduit 7.

Exhaust system 1 comprises an oxidizing catalytic converter (pre-cat) 8 located along exhaust conduit 7, close to turbocharger 3; a particulate filter 9 located along exhaust conduit 7, downstream from pre-cat 8; and a further oxidizing catalytic converter (Front-cat) 10 located along exhaust conduit 7, upstream from particulate filter 9.

Alternatively, the functions of Front-cat 10 and particulate filter 9 may be performed by a single component known as a catalyzed particulate filter (not shown).

Particulate filter 9, whether it be separate from or integrated with Front-cat 10, may be provided with chemical components for reducing particulate combustion temperature.

Exhaust system 1 also comprises an electronic control system 11 for, among other things, determining the total amount of fuel injected into the engine at each cycle.

More specifically, electronic control system 11 comprises an airflow measuring device (debimeter) 12 located along air intake conduit 5 and generating a signal indicating airflow along air intake conduit 5; a differential pressure sensor 13 having a first and a second input connected close to the inlet of Front-cat 10 and the outlet of particulate filter 9 respectively, and an output supplying a pressure drop signal which, by means of the method described in the present invention, can be related to the amount of particulate accumulated in particulate filter 9; a first temperature sensor 14 located at the outlet of particulate filter 9 and supplying a first temperature signal indicating the temperature of the exhaust gas at the outlet of particulate filter 9; a second temperature sensor 15 located at the inlet of particulate filter 9 and supplying a second temperature signal indicating the temperature of the exhaust gas at the inlet of particulate filter 9; a sensor 16 for measuring atmospheric pressure; and an electronic central control unit 17 connected to the aforementioned sensors and implementing the method, described below, according to the invention.

Alternatively, second temperature sensor 15 may also be connected to the outlet of pre-cat 8.

The present invention is the result of in-depth research by the Applicant into the possibility of defining a particulate filter model which is more reliable than known models, and which can actually be implemented in engine central control units currently used in the automotive industry.

More specifically, the Applicant's research is based on the assumption that the assumption on which known models are based—i.e. that particulate distribution in the particulate filter channels and the physical-chemical properties of the particulate remain constant, independently of variations in the operating condition of the engine and in past accumulation—is wrong.

Assuming, therefore, that particulate distribution in the particulate filter channels and the physical-chemical properties of the particulate vary depending on possible variations in the operating condition of the engine and in past accumulation, the Applicant's research has led to the definition of the following equation (eq. 2) which relates the pressure drop across the particulate filter, exhaust gas temperature and flow, and the amount of particulate accumulated in the particulate filter, by means of four test parameters $\alpha,\beta,\gamma,\delta$:

$$\Delta P_{DPF} \cdot \left( \frac{\Delta P_{DPF}}{2} + P_{atm} \right) = T^{\delta+1} \cdot Q_m \cdot (\alpha \cdot \beta \cdot m_S) + \gamma \cdot T \cdot Q_m^2 \quad \text{(eq. 2)}$$

where:
$\Delta P_{DPF}, P_{atm}, T, Q_m$ are respectively the pressure drop across the particulate filter, the absolute pressure downstream from the particulate filter (which may be considered roughly equal to atmospheric pressure), exhaust gas temperature, and exhaust gas flow (which can be calculated by adding engine air intake and the total amount of fuel injected);
$m_S$ is the amount of particulate accumulated in the particulate filter; and
$\alpha,\beta,\gamma,\delta$ are the aforementioned four test operating parameters.

From the above equation, the amount of particulate accumulated in the particulate filter can therefore be calculated easily as follows:

$$m_S = \frac{\Delta P_{DPF} \cdot \left( \frac{\Delta P_{DPF}}{2} + P_{atm} \right) - \gamma \cdot T \cdot Q_m^2}{T^{\delta+1} \cdot Q_m \cdot \beta} - \frac{\alpha}{\beta}$$

More specifically, as regards the four test parameters $\alpha,\beta,\gamma,\delta$:
  $\alpha,\gamma$ depend on Front-cat and particulate filter geometry, and on the properties, such as porosity, pore size, etc., of the particulate filter material;
  $\beta$ depends on particulate filter geometry, particulate axial and radial spatial distribution in the channels, and particulate physical-chemical properties (e.g. density and permeability); and
  $\delta$ is the exponential term of the correlation between exhaust gas temperature and viscosity: typically 0.65–0.74.

For each type of particulate filter, the values of parameters $\alpha,\beta,\gamma,\delta$ can be determined by specific bench tests with the engine at steady operating speed.

More specifically, the values of operating parameters $\alpha,\gamma,\delta$ can be determined by the above tests using a clean particulate filter, i.e. with no particulate, wherein $m_S=0$, while the values of parameter $\beta$ can be determined by the above tests using a particulate filter containing a predetermined amount of particulate, e.g. 7 g/dm$^3$ and 10 g/dm$^3$.

More specifically, the above tests substantially comprise determining the time pattern of the pressure drop across the particulate filter, exhaust gas temperature and exhaust gas flow in the above particulate loading conditions, and calculating the values of parameters $\alpha,\beta,\gamma,\delta$ whereby the time pattern of $\Delta P_{DPF}$ determined by the proposed equation corresponds as closely as possible to the test-determined pattern.

The particulate filter model must be validated in a wide range of engine operating conditions, e.g. at idling speed, in conditions corresponding to urban, extra-urban, and motorway driving, and in high-torque and high-power conditions.

The proposed model is valid for any axial and radial particulate distribution in the particulate filter channels, by the distribution and physical-chemical properties of the particulate, as stated, being accounted for in the value of parameter $\beta$. This, in fact, is the only one of the four test parameters which, in the proposed equation, multiplies the amount of particulate accumulated $m_S$, and actually relates the pressure drop $\Delta P_{DPF}$ across the particulate filter to the amount of particulate accumulated $m_S$.

The proposed equation provides for obtaining a particulate filter model in which particulate distribution in the particulate filter channels is assumed variable as a function of engine operating conditions and past particulate accumulation in the particulate filter.

More specifically, operating parameter $\beta$ is mapped as a function of different engine operating conditions, i.e. in particular steady particulate accumulation conditions.

Tests conducted by the Applicant have led to the following assumption concerning the relationship between the values assumed by operating parameter $\beta$ and different engine operating conditions.

Different particulate distributions in each of the particulate filter channels and/or different physical-chemical properties (e.g. permeability and density) of the particulate are discernible, and each relatable to a specific engine operating condition, i.e. a particular steady accumulation condition, which can be identified on the so-called "engine map", defined by engine speed and brake mean effective pressure (BMEP).

Figure 2A:
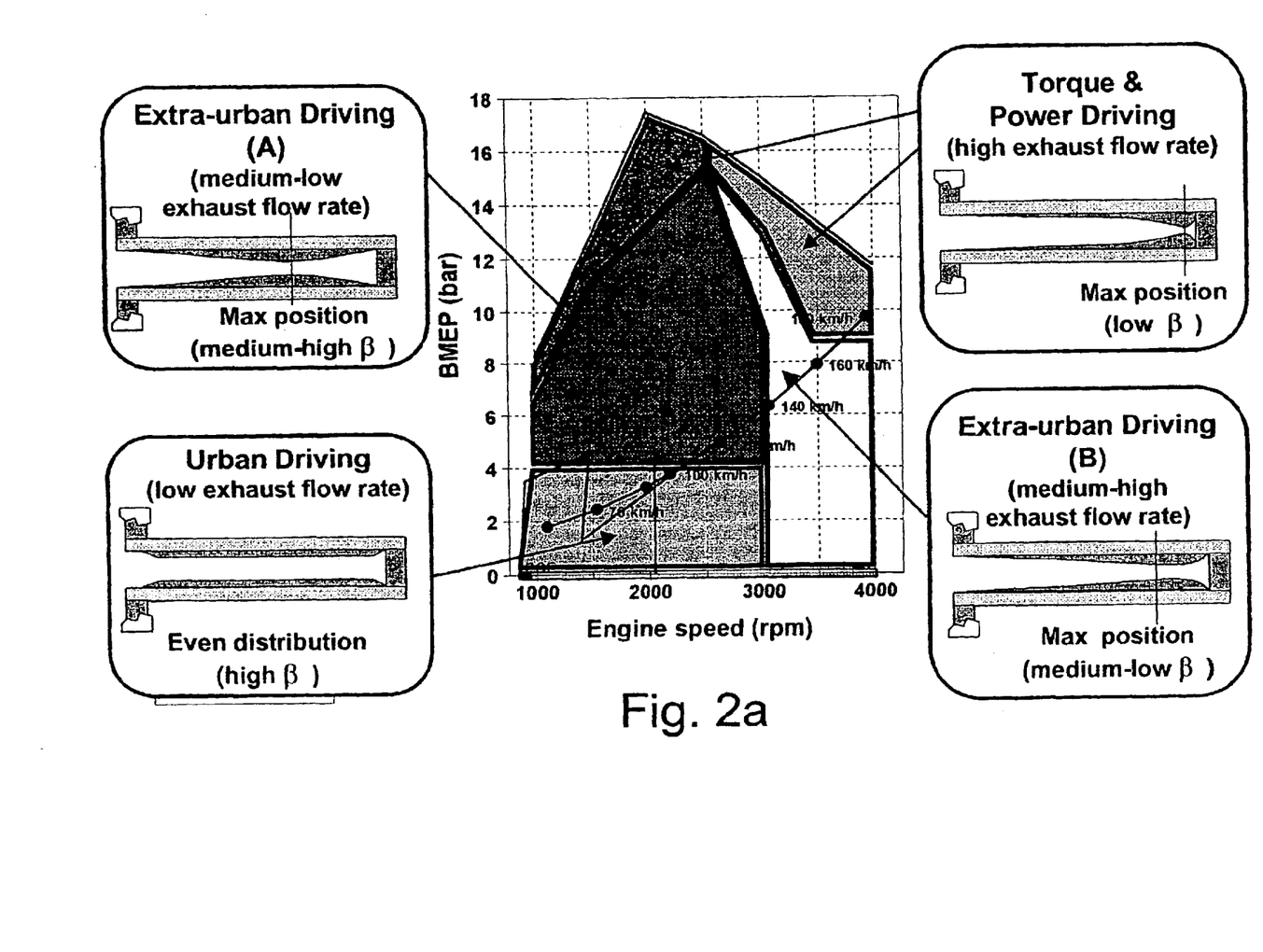
FIG. 2a shows, schematically, possible variations in particulate distribution in the particulate filter channels in different engine operating conditions.

FIG. 2a shows, by way of example, four possible distributions of a constant amount of particulate in each of the particulate filter channels, the relative engine operating conditions, the engine map areas corresponding to the engine operating conditions, and the relative qualitative values of parameter $\beta$.

As can be seen:
  in a urban driving condition, in which the engine substantially operates in the bottom left region of the engine map, and exhaust gas flow and temperature are low, particulate tends to accumulate evenly in the channels, thus giving a high parameter $\beta$ value (a constant amount of particulate corresponds to a high pressure drop across the particulate filter);

in a first extra-urban driving condition (A), in which the engine substantially operates in the middle region of the engine map, and exhaust gas flow and temperature are medium-low, particulate tends to accumulate predominantly halfway along the channels, thus giving a medium-high parameter β value (a constant amount of particulate corresponds to a medium-high pressure drop across the particulate filter);

in a second extra-urban driving condition (B), in which the engine substantially operates in the bottom right region of the engine map, and exhaust gas flow and temperature are medium-high, particulate tends to accumulate at the end of the channels, thus giving a medium-low parameter β value (a constant amount of particulate corresponds to a medium-low pressure drop across the particulate filter);

in a torque and power driving condition, in which the engine substantially operates in the top region of the engine map, and exhaust gas flow and temperature are high, particulate tends to accumulate substantially at the end of the channels, thus giving a low parameter β value (a constant amount of particulate corresponds to a low pressure drop across the particulate filter).

Figure 2B:
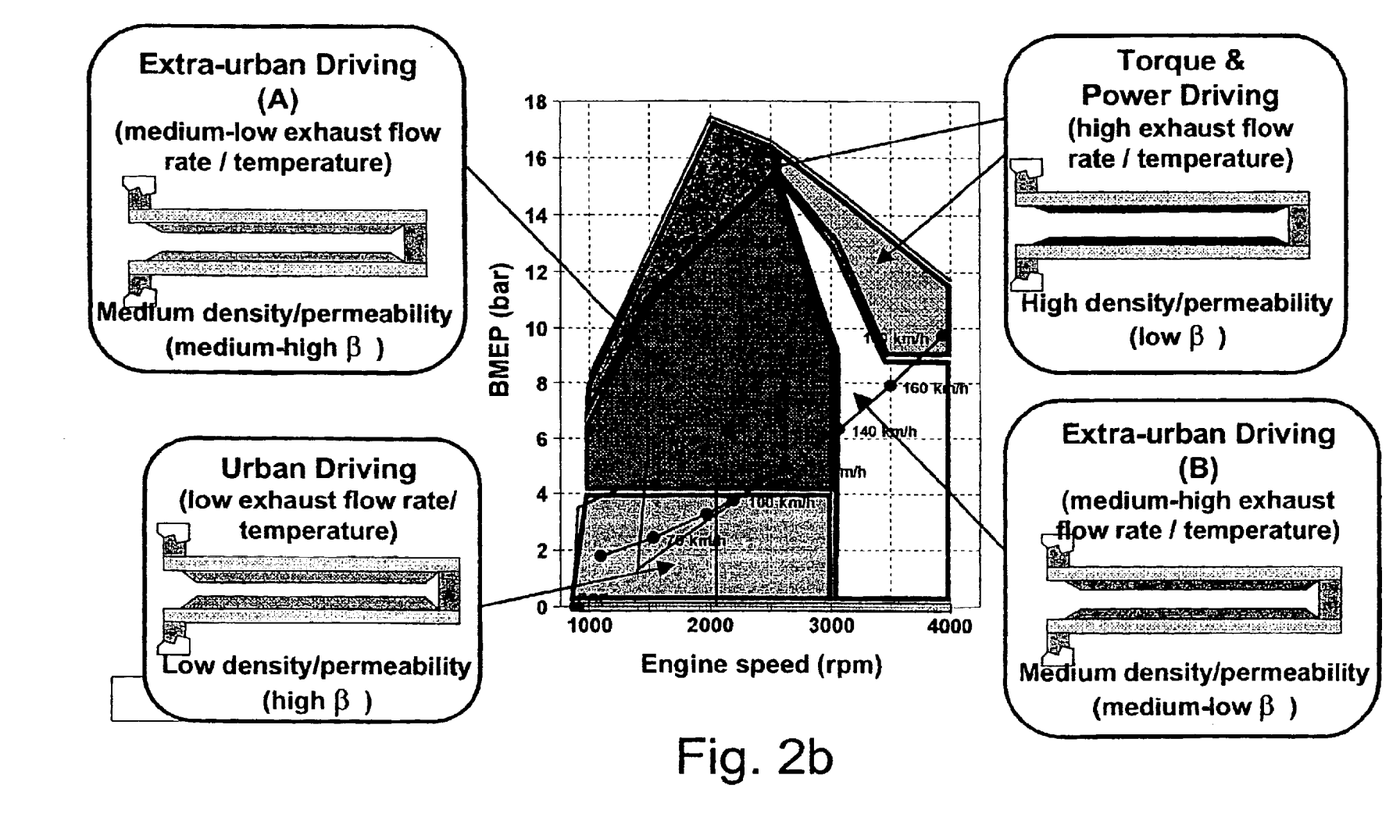
FIG. 2b shows, schematically, possible variations in the physical-chemical properties of the particulate accumulated in the particulate filter channels in different engine operating conditions.

Similarly, FIG. 2b shows, by way of example, four possible physical property values of a constant amount of particulate, the relative engine operating conditions, the engine map areas corresponding to the engine operating conditions, and the relative qualitative values of parameter β.

As can be seen:

in a urban driving condition, in which the engine substantially operates in the bottom left region of the engine map, and exhaust gas flow and temperature are low, the accumulated particulate is characterized by low density and permeability values, thus giving a high parameter β value (a constant amount of particulate corresponds to a high pressure drop across the particulate filter);

in a first extra-urban driving condition (A), in which the engine substantially operates in the middle region of the engine map, and exhaust gas flow and temperature are medium-low, the accumulated particulate is characterized by medium-low density and permeability values, thus giving a medium-high parameter β value (a constant amount of particulate corresponds to a medium-high pressure drop across the particulate filter);

in a second extra-urban driving condition (B), in which the engine substantially operates in the bottom right region of the engine map, and exhaust gas flow and temperature are medium-high, the accumulated particulate is characterized by medium-high density and permeability values, thus giving a medium-low parameter β value (a constant amount of particulate corresponds to a medium-low pressure drop across the particulate filter);

in a torque and power driving condition, in which the engine substantially operates in the top region of the engine map, and exhaust gas flow and temperature are high, the accumulated particulate is characterized by high density and permeability values, thus giving a low parameter β value (a constant amount of particulate corresponds to a low pressure drop across the particulate filter).

Given the above assumptions, based on test data, concerning particulate distribution and the variation in physical-chemical properties, the following deductions can be made:

a) as exhaust gas flow rate and temperature increase, the, particulate has a greater tendency to accumulate towards the end of the particulate filter channels and/or to be characterized by high density and permeability values, so that the parameter β value is lower, and vice versa;

b) particulate distribution and physical-chemical properties are irreversibly sensitive to exhaust gas flow rate and temperature:

b1) if the particulate has accumulated in a low exhaust gas flow rate and temperature condition, and the engine switches to full-power operation (high flow rate and temperature), the particulate already accumulated tends to shift towards the end of the channels and/or to be characterized by higher permeability and density values (the particulate is compressed on the filter walls) in a time depending on engine operating conditions;

b2) if part of the particulate is accumulated in a high exhaust gas flow rate and temperature condition, which then switches to a low exhaust gas flow rate and temperature condition, particulate distribution, depending on the amount of particulate accumulated in the new condition, tends to equal the total distribution of both conditions; and/or the accumulated particulate, depending on the amount of particulate accumulated in the new condition, tends to be characterized by intermediate permeability and density values between the two conditions.

Figure 3A:
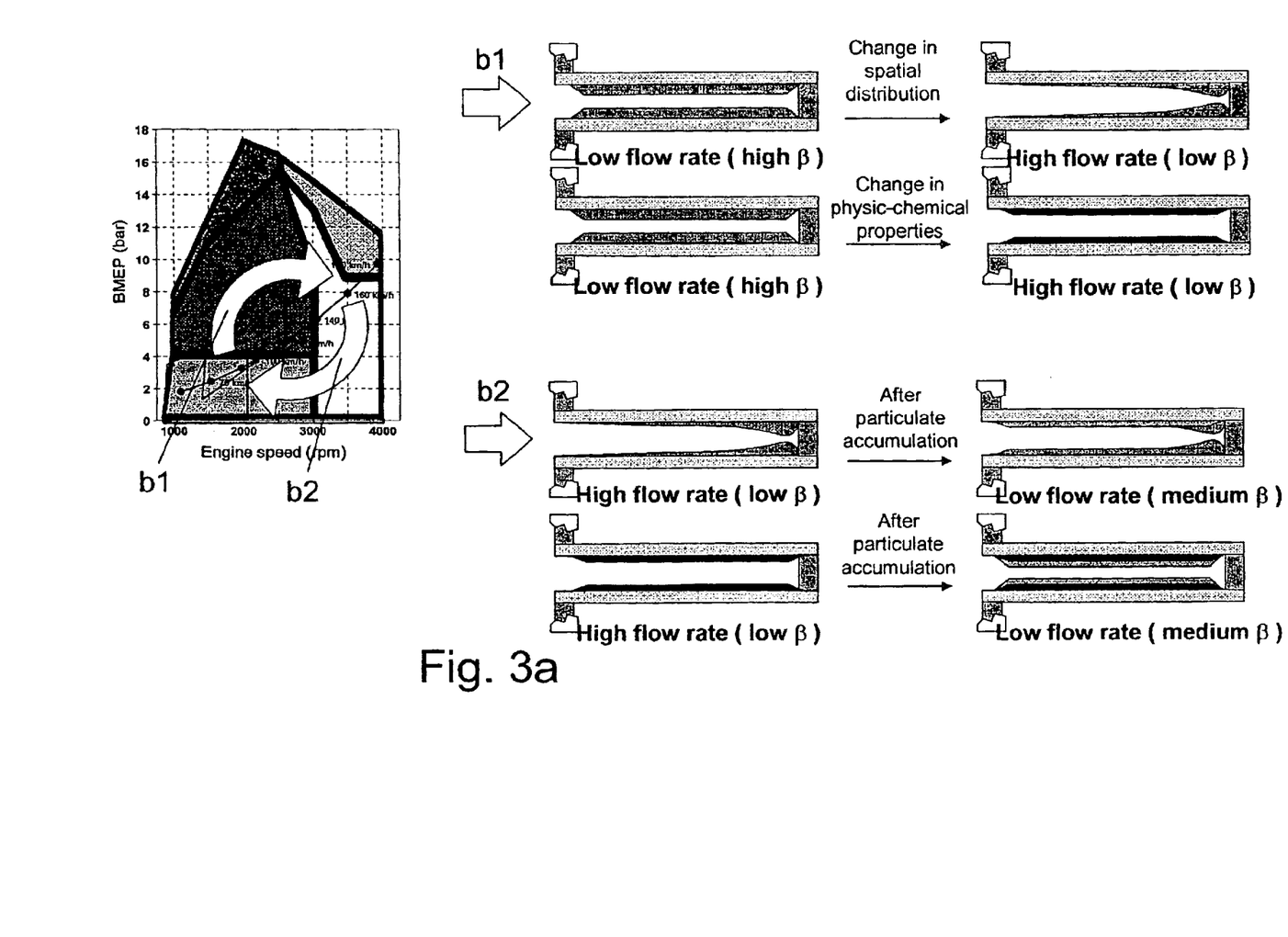
FIG. 3a shows, schematically, the variation in distribution and physical-chemical properties of the particulate in the particulate filter channels depending on possible variations in engine operating conditions.

The assertions in b1) and b2) are shown schematically in FIG. 3a, which also shows an example engine map in which the passage from a low exhaust gas flow rate and temperature condition to a high exhaust gas flow rate and temperature condition, and vice versa, is indicated by arrows b1 and b2 respectively.

The above assumptions concerning the relationship between parameter β values and particulate distribution in the particulate filter channels can be implemented at engine control unit level, for example, as follows:

a matrix of reference parameter β values, depending on the engine operating condition, i.e. a steady accumulation condition of the particulate in the particulate filter, and hereinafter indicated $\beta_{MAP}$, is generated and memorized in map form;

the reference value $\beta_{MAP}$ of parameter β indicating the current engine operating condition is compared with the parameter β value used previously in the model described by the equation (eq. 2) to calculate the amount of particulate accumulated, and which is hereinafter indicated $\beta_{MOD\_OLD}$;

if $\beta_{MAP} \leq \beta_{MOD\_OLD}$, e.g. as a result of switching from a urban to extra-urban driving condition, then reference value $\beta_{MAP}$ is used—after a characteristic time interval varying as a function of engine operating conditions—in the model described by the equation (eq. 2) to calculate the amount of particulate accumulated, so that $\beta_{MOD} = \beta_{MAP}$ (the particulate shifts towards the end of the particulate filter channels and/or tends to be compressed, i.e. characterized by higher permeability and density values);

if $\beta_{MAP} > \beta_{MAP\_OLD}$, e.g. as a result of switching from an extra-urban to urban driving condition, then the last estimated value of the amount of particulate accumulated in the particulate filter—hereinafter indicated $m_{S\_OLD}$—is memorized, and, when the amount of particulate accumulated after the switch between the two driving conditions ($m_S - m_{S\_OLD}$) exceeds a given threshold value, a new operating value $\beta_{MOD}$ of parameter $\beta$ to be used in the model described by the equation (eq. 2) is calculated according to the equation:

$$\beta_{MOD} = \beta_{MAP} - \frac{m_{S\_OLD}}{m_S} \cdot (\beta_{MAP} - \beta_{MOD\_OLD}) \quad \text{(eq. 3)}$$

As can be seen:

if $m_S = 2 \cdot m_{S\_OLD}$, i.e. the amount of particulate accumulated in the new condition is the same as in the previous condition, then $$\beta_{MOD} = \frac{\beta_{MAP} + \beta_{MOD\_OLD}}{2}$$

(an arithmetic mean of the reference parameter $\beta$ values of the two driving conditions is used);

if $m_S \gg m_{S\_OLD}$, i.e. the amount of particulate accumulated in the new condition is much higher than in the previous condition, then $\beta_{MOD} = \beta_{MAP}$ (the reference parameter $\beta$ value of the new driving condition is used);

The amount of particulate accumulated in the particulate filter is therefore calculated as a function of engine operating conditions and also past particulate accumulation in the particulate filter.

At this point, regeneration of the particulate filter can be activated either simply on the basis of the amount of particulate accumulated in the particulate filter, or more accurately also on the basis of a particulate state index $I_{PART}$ (i.e. defined in terms of particulate distribution uniformity, or the state of the relative physical-chemical properties) calculated as a function of the operating value $\beta_{MOD}$ of parameter $\beta$ according to the equation:

$$I_{PART} = \frac{\beta_{MAX} - \beta_{MOD}}{\beta_{MAX} - \beta_{MIN}} \quad 0 < I_{PART} < 1 \quad \text{(eq. 4)}$$

where $\beta_{MAX}$ and $\beta_{MIN}$ are the maximum and minimum parameter $\beta$ values memorized in the reference value $\beta_{MAP}$ map.

The particulate distribution uniformity index $I_{PART}$ provides for accurately determining the extent to which distribution or the state of the physical-chemical properties of the particulate in the particulate filter is critical, and its effect on the pressure drop across the particulate filter. That is, as the $I_{PART}$ value increases, the more critical regeneration of the particulate filter becomes.

In the following two cases, for example:

1) a power and torque driving condition, in which exhaust gas flow and temperature are high: particulate accumulates mainly at the end of the particulate filter channels and/or is characterized by high density and permeability values, thus giving a low operating value of parameter $\beta$;

2) an extra-urban driving condition, in which exhaust gas flow and temperature are medium-low: particulate accumulates mainly halfway along the particulate filter channels and/or is characterized by medium-low density and permeability values, thus giving a medium-high operating value of parameter $\beta$;

For a given amount of accumulated particulate, the first of these two engine operating conditions is much more critical than the second, and is reflected in the $I_{PART}$ value: in the first case, in fact, $I_{PART} \approx 1$, whereas in the second, $I_{PART} \approx 0.5$.

To sum up, a relationship has been shown to exist either between the parameter $\beta$ values and particulate distribution in each of the particulate filter channels, or between the parameter $\beta$ values and the physical-chemical properties of the particulate, or both simultaneously to a different extent.

In other words, depending on variations in engine operating conditions, particulate distribution in the particulate filter channels may vary, while the relative physical-chemical properties remain constant, or may remain substantially unchanged and it is the physical-chemical properties of the particulate which vary.

What has been said above concerning mapping and calculating the operating values of parameter $\beta$ as a function of engine operating conditions applies to both situations or any situations in between.

Figure 3B:
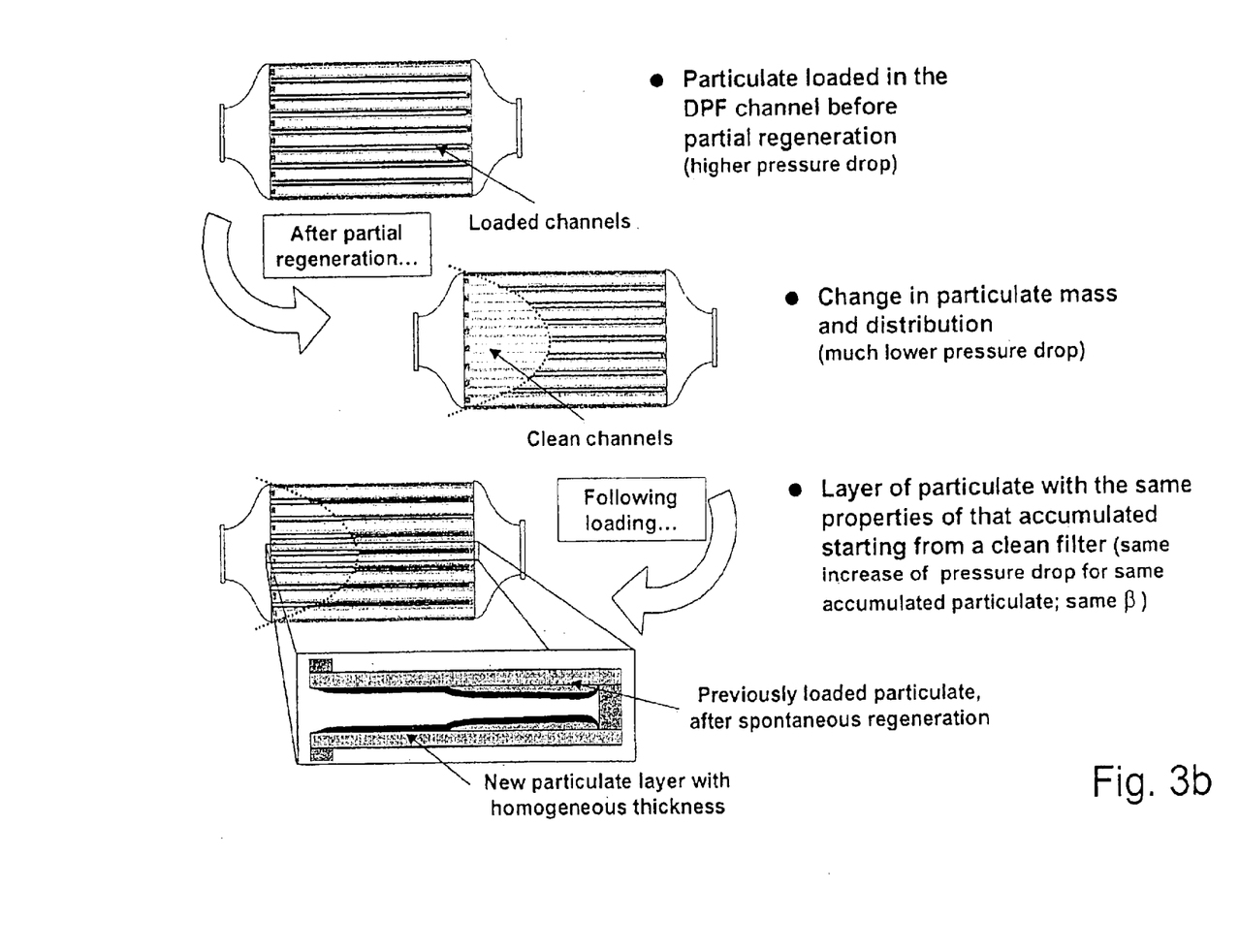
FIG. 3b shows, schematically, the variation in distribution and physical-chemical properties of the particulate in the particulate filter channels after partial regenerations (e.g. NOx-based spontaneous regenerations) and subsequent accumulation.
Figure 3C:
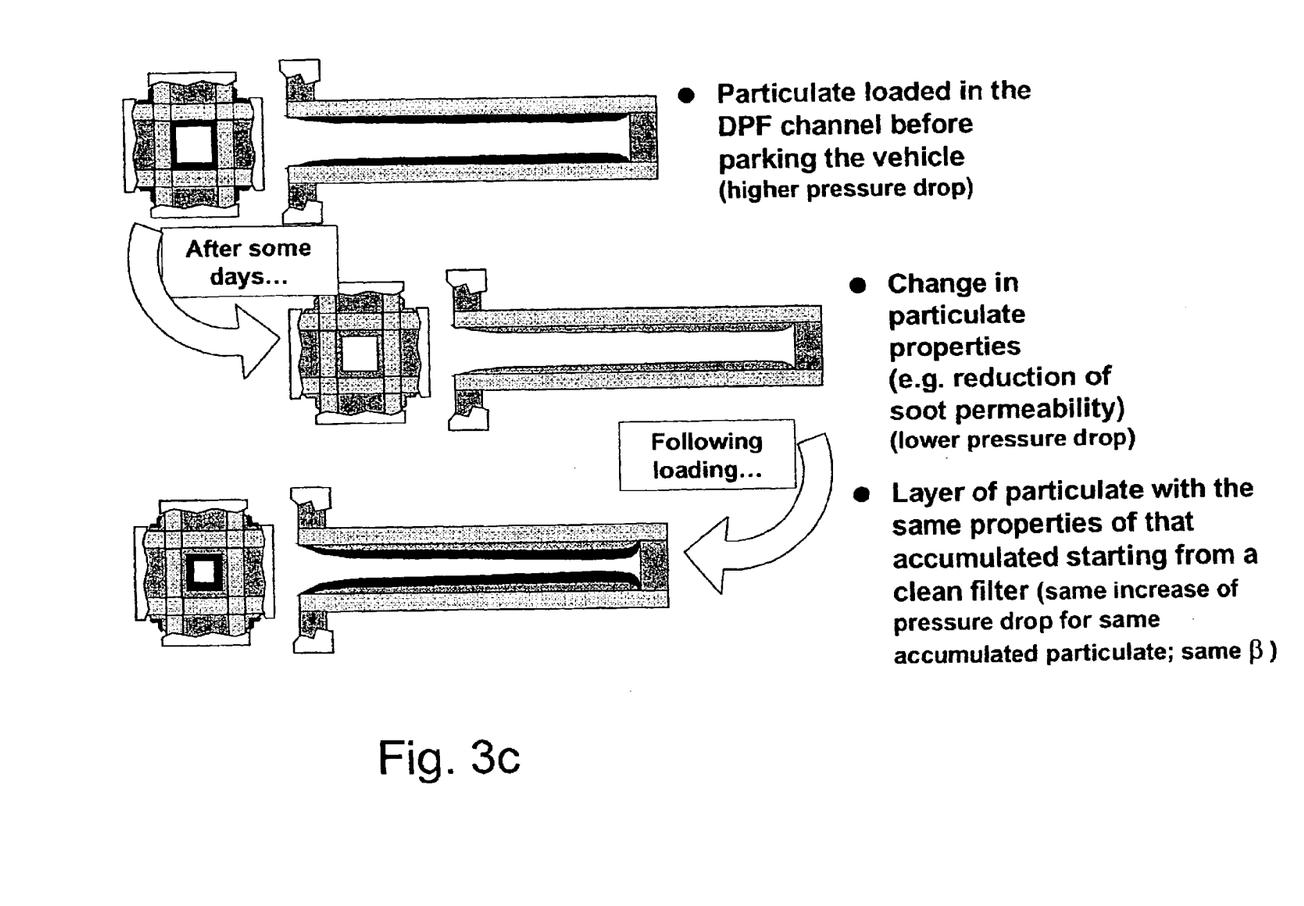
FIG. 3c shows, schematically, the variation in physical-chemical properties of the particulate in the particulate filter channels after prolonged vehicle disuse ("parking" effect) and subsequent accumulation.

In order to take into account the effects of partial regenerations (e.g. NOx-based spontaneous regeneration) and prolonged vehicle disuse ("parking" effect), a specific algorithm has been defined. It is known that after partial regenerations or prolonged vehicle disuse, the distribution and/or physical-chemical properties of particulate can change, resulting in a different (typically lower) pressure drop through the filter at the same exhaust gas flow and temperature, with the same particulate mass accumulated in the filter. Nevertheless, tests conducted by the Applicant have demonstrated that the subsequently accumulated particulate is not influenced by the residual one already present in the filter. In other words, the subsequently accumulated particulate is characterised by the same physical-chemical properties and distribution of that accumulated starting from a clean filter in the same engine operating conditions (it means that it is characterised by same value of $\beta$). These phenomena are shown schematically in FIGS. 3b and 3c.

Therefore, an offset $\Delta m$ can be calculated in order to correct (typically increase) the particulate mass accumulated in the filter $m_S$, estimated without considering the effects of partial regenerations (e.g. NOx-based spontaneous regeneration) and prolonged vehicle disuse ("parking" effect), according to equation 5, $$m_{S\_CORR} = m_S + \Delta m \quad \text{(eq. 5)}$$

where $m_{S\_CORR}$ is the actual mass of particulate accumulated in the filter. The offset $\Delta m$ is determined in the following cases:

1) After an certain waiting time subsequent to the engine switching on, the current value of $m_S$ is subtracted (if lower) to the value of $m_{S\_CORR}$ stored in the electronic control unit at the previous key-off ($m_{S\_CORR\_ECU}$): $\Delta m = m_{S\_CORR\_ECU} - m_S$. It allows to compensate the change in physical-chemical properties of particulate after a prolonged vehicle disuse ("parking" effect).

2) After a partial regeneration (e.g. NOx-based spontaneous regeneration), the current value of $m_S$ is subtracted (if lower) to the current value of $m_{S\_CORR}$: $\Delta m = m_{S\_CORR} - m_S$. The current value of $m_{S\_CORR}$ is evaluated as difference between the value of $m_{S\_CORR}$ before starting the regeneration and an experimentally estimated value of regenerated particulate $m_{REG}$ (a function of time and engine operating conditions). It allows to compensate the change in particulate distribution after a partial regeneration (e.g. NOx-based spontaneous regeneration).

Once the offset $\Delta m$ is evaluated, it is added to the current value of $m_S$, so that $m_{S\_CORR} = m_S + \Delta m$.

Finally, the value of m is considered reliable only if the value of exhaust gas flow and pressure drop through the filter are higher than certain acceptable values, in order to limit the effects of the typically limited sensors' accuracy (measurement in idle conditions are usually considered as not reliable). If the value of exhaust gas flow and pressure drop through the filter are lower than certain acceptable values, a simulation state is activated (Sim=on), and the last acceptable value of $m_{S\_CORR}$ is incremented at every time step with an experimentally estimated instantaneous value of particulate emission $m_{EXP}$ (a function of the engine operating conditions).

Figure 4:
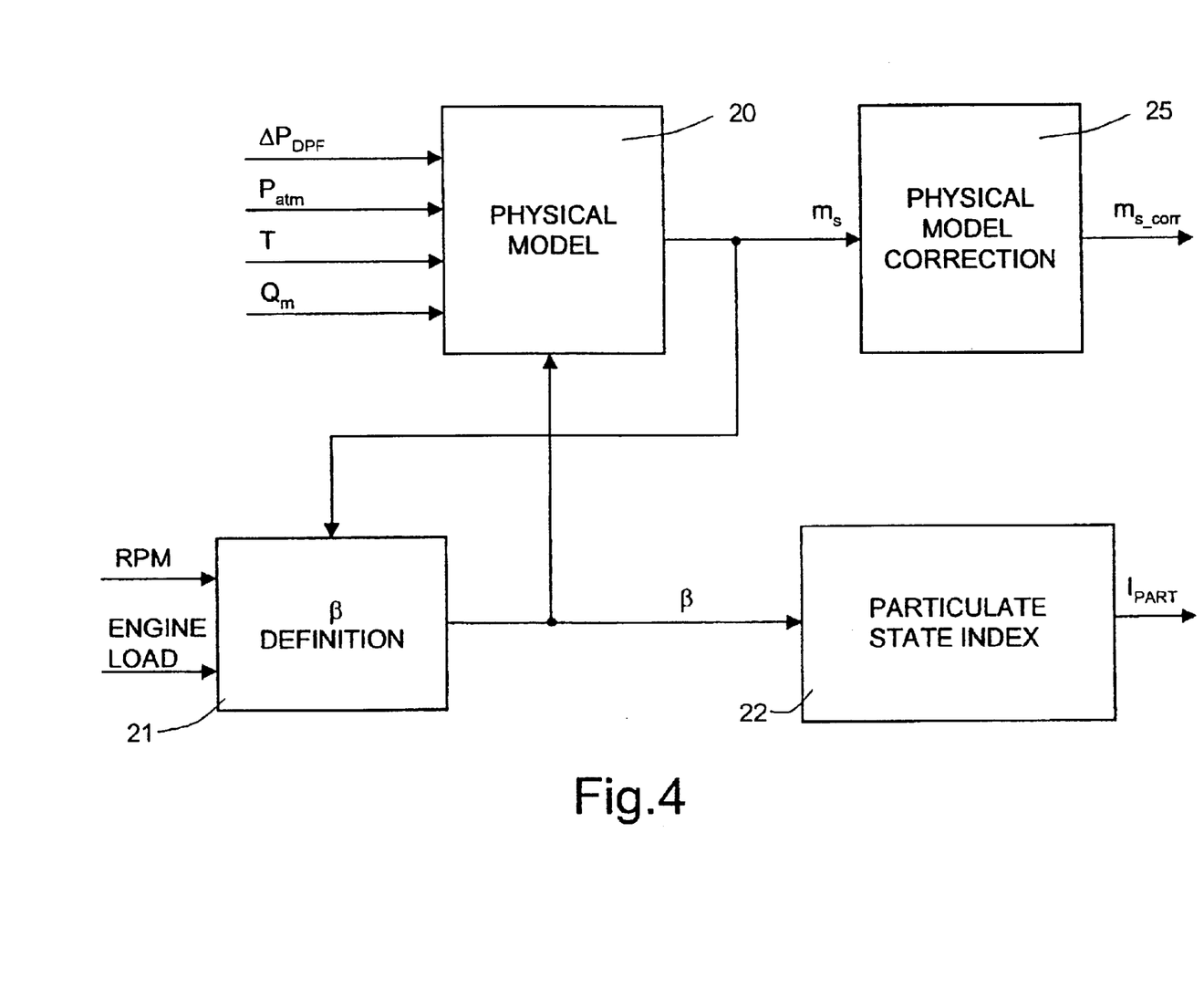
FIG. 4 shows a block diagram of the particulate filter model according to the invention.

The FIG. 4 block diagram sums up what has been said so far concerning estimating the amount of particulate accumulated in the particulate filter, and activating regeneration of the filter.

More specifically, in FIG. 4, number 20 indicates the block implementing the physical model of the particulate filter described in the equation illustrated previously (eq. 2), and which supplies the amount of particulate accumulated in the particulate filter; 21 indicates the block supplying the operating value $\beta_{MOD}$ of parameter $\beta$ to be used in block 20 and relative to the current engine operating condition and past particulate accumulation in the particulate filter; and 22 indicates the block calculating particulate state index $I_{PART}$.

More specifically, block 20 receives the pressure drop $\Delta P_{DPF}$ across the particulate filter, exhaust gas temperature T, exhaust gas flow $Q_m$, atmospheric pressure $P_{atm}$, and the operating value $\beta_{MOD}$ of parameter $\beta$ supplied by block 21, and supplies the amount of particulate $m_S$ accumulated in the particulate filter in the current engine operating condition, and which is calculated using the above equation (eq. 2).

Block 21 receives the engine speed and load defining the current engine operation condition, receives from block 20 the amount of particulate $m_S$ accumulated in the particulate filter, and supplies the operating value $\beta_{MOD}$ of parameter $\beta$ to block 20 to calculate the amount of accumulated particulate $m_S$, and to block 22 to calculate particulate state index $I_{PART}$.

Block 22 receives the operating value $\beta_{MOD}$ of parameter $\beta$ from block 21, and supplies the state index $I_{PART}$ of the particulate in the particulate filter.

Finally, block 25 receives amount of particulate $m_S$ accumulated in the particulate filter, estimated without considering the effects of partial regenerations (e.g. NOx-based spontaneous regeneration) and prolonged vehicle disuse ("parking" effect), and supplies the final corrected mass $m_{S\_CORR}$ of particulate accumulated in the filter.

Figure 5:
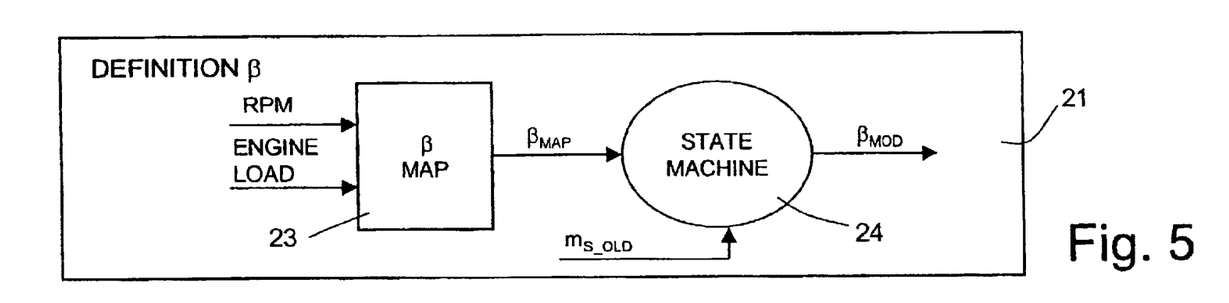
FIG. 5 shows a more detailed block diagram of the "β definition" block in FIG. 4.
Figure 6:
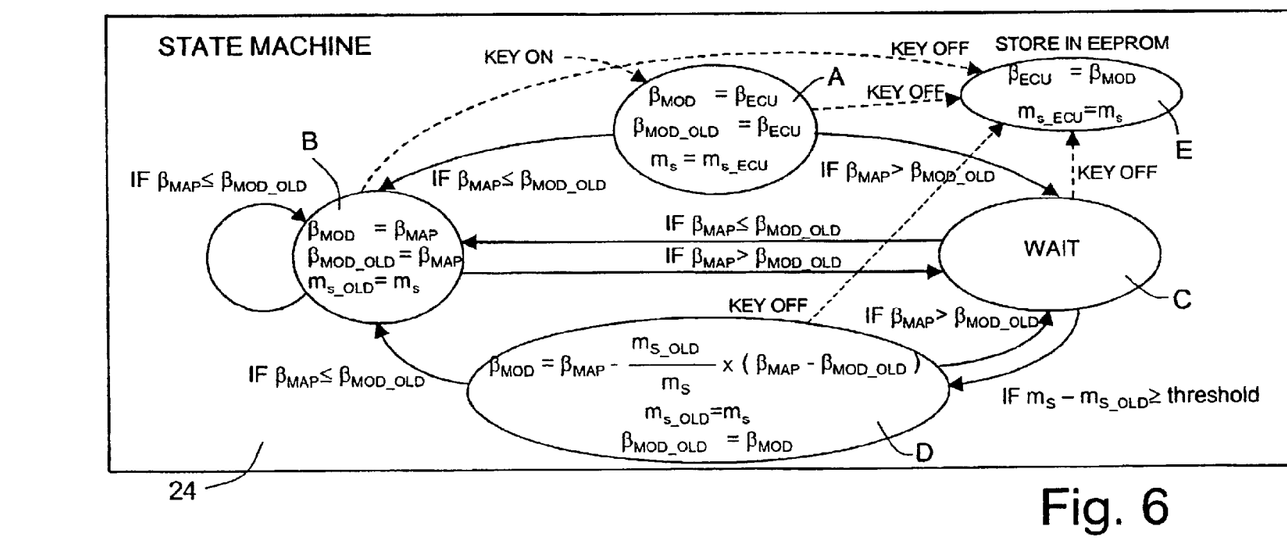
FIG. 6 shows a state diagram of a state machine in FIG. 5.

FIGS. 5 and 6 show a block diagram and state diagram illustrating the operations performed in block 21 in FIG. 4 to calculate the operating value $\beta_{MOD}$ of parameter $\beta$ to be used to estimate the amount of particulate accumulated in the particulate filter.

More specifically, in FIG. 5, number 23 indicates the block storing the map of reference values $\beta$MAP of parameter $\beta$ as a function of engine operating conditions, and which receives the engine speed and load, and supplies the reference value $\beta_{MAP}$ of parameter $\beta$ relative to the current engine condition; and number 24 indicates a state machine for calculating the operating value $\beta_{MOD}$ of parameter $\beta$, and which receives reference value $\beta_{MAP}$ from block 23 and the memorized amount of particulate $m_{S\_OLD}$, and supplies operating value $\beta_{MOD}$.

State machine 24 performs the operations described below with reference to the state diagram in FIG. 6.

As shown in FIG. 6, turn-on of the engine corresponds to a state A in which $\beta_{MOD}=\beta_{ECU}$, $\beta_{MOD\_OLD}=\beta_{ECU}$ and $m_S=m_{S\_ECU}$, where $\beta_{ECU}$ and $m_{S\_ECU}$ are the parameter $\beta$ and accumulated particulate mass $m_S$ values used in the model before the engine was last turned off and memorized in the engine control unit.

If $\beta_{MAP} \leq \beta_{MOD\_OLD}{}^{LD}$, then state A goes to state B in which the last estimated value of accumulated particulate $m_S$ is memorized by entering $m_{S\_OLD}=m_S$, and $\beta_{MOD}=\beta_{MAP}$ and $\beta_{MOD\_OLD}=\beta_{MAP}$ are entered; whereas, if $\beta_{MAP}>\beta_{MOD\_OLD}$, state A goes to a standby state C. In state B, if $\beta_{MAP}>\beta_{MOD\_OLD}$, state B goes to state C; whereas, if $\beta_{MAP} \leq \beta_{MOD\_OLD}$, state B holds.

In state C, if $\beta_{MAP} \leq \beta MOD_{\_OLD}$, state C goes to state B; whereas, if the calculated accumulated particulate $m_S$ exceeds the memorized accumulated particulate $m_{S\_OLD}$ by a predetermined threshold, i.e. if $m_S-m_{S\_OLD} \geq$ threshold, state C goes to a state D in which value $\beta_{MOD}$ of parameter $\beta$ is calculated according to the equation shown previously (eq. 3), and $\beta_{MOD\_OLD}=\beta_{MOD}$ and $m_{S\_OLD}=m_S$ are entered.

In state D, if $\beta_{MAP}>\beta_{MOD\_OLD}$, state D goes back to state C; whereas, if $\beta_{MAP} \leq \beta_{MOD\_OLD}$, state D goes to state B.

When the engine is turned off, any state A, B, C, D goes to state E, in which the current $\beta_{MOD}$ and $m_S$ values are memorized in the engine control unit as $\beta_{ECU}$ and $m_{S\_ECU}$ respectively, so that they are available the next time the engine is turned on.

Figure 7:
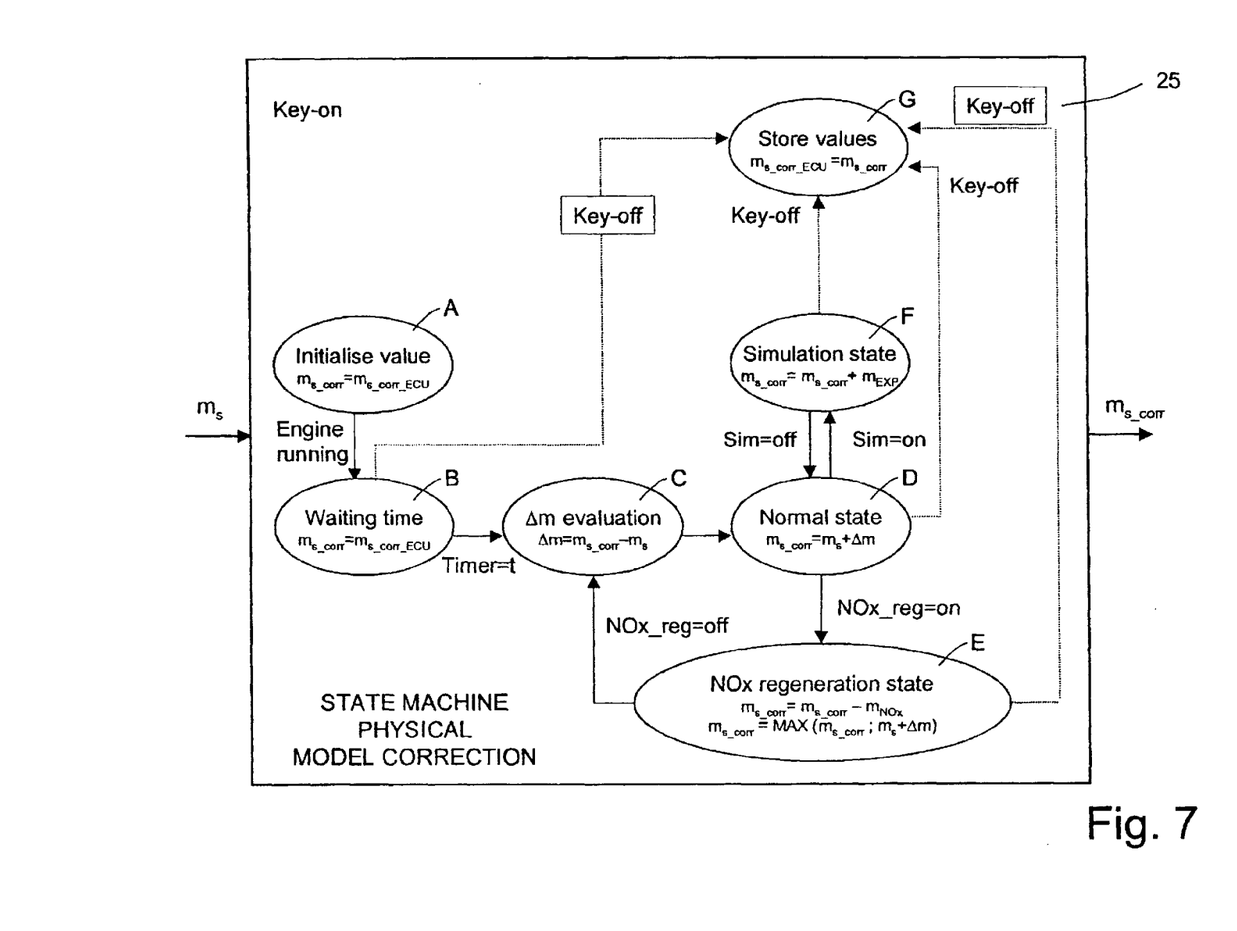
FIG. 7 shows a more detailed diagram of the "Phisical Model correction" block in FIG. 4.

FIG. 7 shows a state diagram illustrating the operations performed in block 25 in FIG. 4 to calculate the final corrected value of particulate mass accumulated in the filter $m_{S\_CORR}$.

As shown in FIG. 7, turn-on of the engine corresponds to a state A in which $m_{S\_CORR}=m_{S\_CORR\_ECU}$, where $m_{S\_CORR\_ECU}$ is the value of accumulated particulate mass $m_{S\_CORR}$ before the engine was last turned off and memorized in the engine control unit.

After an certain waiting time (state B) subsequent to the engine switching on, i.e. when the timer reach the value t, the current value of $m_S$ is subtracted (if lower) to the value of $m_{S\_CORR}$ stored in the electronic control unit at the previous key-off ($m_{S\_CORR\_ECU}$), calculating an offset value: $\Delta m = m_{S\_CORR}-m_S$ (state C).

The offset $\Delta m$ is added to the subsequent values of $m_S$ in normal state: $m_{S\_CORR}=m_S+\Delta m$ (state D). This part of the state machine is able to take into account possible variations of in spatial distribution of the particulate in the particulate filter and/or variations in the physical-chemical properties of the particulate, between two subsequent key-off and key-on (i.e. parking of the vehicle).

The offset correction (state D) is performed only if the value of $m_S$ is considered reliable, i.e. if the variable Sim=off. It means that the value of exhaust gas flow and pressure drop through the filter are higher than certain acceptable values. If Sim=on, a simulation state is activated (State F), and the output of the state machine $m_{S\_CORR}$ is incremented at every time step with an experimentally estimated instantaneous value of particulate emission $m_{EXP}$ (a function of the engine operating conditions).

If a NOx-based spontaneous regeneration state is recognized, i.e. NOx_reg=on (NOx_reg is a function of the engine operating conditions), the state E is activated, and the output of the state machine $m_{S\_CORR}$ is decremented at every time step with an experimentally estimated instantaneous value of particulate regenerated $m_{NOx}$ (a function of the engine operating conditions). Then, $M_{S\_CORR}$ is calculated as the maximum between its value and the value of $m_S+\Delta m$ (i.e. the value of $m_{S\_CORR}$ in state D.

After a NOx-based spontaneous regeneration, i.e. NOx_reg=off, the current value of $m_S$ is subtracted (if lower) to the current value of $m_{S\_CORR}$, calculating an offset value: $\Delta m = m_{S\_CORR}-m_S$ (state C).

This part of the state machine is able is able to take into account possible variations of in spatial distribution of the particulate in the particulate filter and/or variations in the physical-chemical properties of the particulate, due to NOx-based spontaneous regeneration of the filter.

At key-of (state G), the value of $m_{S\_CORR}$ is memorized in the engine control unit ($m_{S\_CORR\_ECU}=m_{S\_CORR}$). The advantages of the present invention will be clear from the foregoing description.

In particular, the present invention provides for calculating the amount of particulate accumulated in the particulate filter using an engine control unit of the type commonly employed in the automotive industry, i.e. with no need for high-power, and therefore high-cost, computing means.

As a result, the present invention enables adoption of the above particulate filter regeneration criteria (on the basis of the actual amount of particulate accumulated, or a particulate state index), which, being more efficient than currently used criteria (vehicle mileage), provide for only regenerating the particulate filter when absolutely necessary, thus minimizing the drawbacks, in terms of fuel consumption and full-load performance, typically associated with particulate filter regeneration.

Tests conducted by the Applicant, in fact, show that, whereas a 10-minute regeneration of the particulate filter may increase fuel consumption by as much as 200%, regenerating the particulate filter as indicated in the present disclosure results in an average fuel consumption increase of only 1–2%.

Moreover, the particulate filter model proposed is based on simple analytical equations, can be validated easily by a specific set of bench tests with the engine operating at steady speed, and, with the exception of temperature and pressure drop sensors, can be implemented with no need for additional sensors other than those normally provided on the vehicle.

Clearly, changes may be made to what is described and illustrated herein without, however, departing from the scope of the present invention as defined in the accompanying claims.

What is claimed is:

1. A method of determining the amount of particulate ($m_S$) accumulated in a particulate filter (9), comprising the step of determining the variation in spatial distribution and accumulation patterns of the particulate along channels in said particulate filter (9) as a function of engine operating conditions and past particulate accumulation in said particulate filter (9), whereby different categories of said accumulation patterns are associated with different engine operating conditions.

2. A method as claimed in claim 1, characterized by comprising the step of determining at least one of the variation in spatial distribution of the particulate in said particulate filter (9) and the variation in the physical-chemical properties of the particulate due to partial regenerations (e.g. NOx-based spontaneous regeneration) and prolonged vehicle disuse ("parking" effect).

3. A method as claimed in claim 1, characterized by also comprising the steps of:

determining a state index ($I_{PART}$) of the particulate in said particulate filter (9); and activating regeneration of said particulate filter (9) on the basis of said state index ($I_{PART}$) of the particulate in said particulate filter (9).

4. A method as claimed in claim 3, characterized in that said state index ($I_{PART}$) of the particulate in said particulate filter (9) is determined according to the following equation:

$$I_{PART} = \frac{\beta_{MAX} - \beta_{MOD}}{\beta_{MAX} - \beta_{MIN}} \quad 0 < I_{PART} < 1$$

where:

$I_{PART}$ is said state index of the particulate;

$\beta_{MOD}$ is said operating value of parameter $\beta$; and $\beta_{MAX}$ and $\beta_{MIN}$ are memorized maximum and minimum values of parameter $\beta$.

5. A method of determining the amount of particulate ($m_S$) accumulated in a particulate filter (9), comprising the steps of:

determining at least one of the variation in spatial distribution of the particulate in said particulate filter (9) and the variation in the physical-chemical properties of the particulate as a function of engine operating conditions and past particulate accumulation in said partical filter (9);

determining at least one of the variation in spatial distribution of the particulate in said particulate filter (9) and the variation in the physical-chemical properties of the particulate as a function of exhaust gas temperature and flow and past particulate accumulation in said partical filter (9).

6. A method of determining the amount of particulate ($m_S$) accumulated in a particulate filter (9), comprising the steps of:

determining at least one of the variation in spatial distribution of the particulate in said particulate filter (9) and the variation in the physical-chemical properties of the particulate as a function of engine operating conditions and past particulate accumulation in said partical filter (9);

determining a number of reference values ($\beta_{MAP}$) of a parameter ($\beta$) defining a relationship between the amount of particulate ($m_S$) accumulated in said particulate filter (9) and the pressure drop ($\Delta P_{DPF}$) across the particulate filter (9), each of said reference values ($\beta_{MAP}$) relating to a respective steady engine operating condition corresponding to a particular steady particulate accumulation condition in the particulate filter (9);

determining an operating value ($\beta_{MOD}$) of said parameter ($\beta$) relative to the current engine operating condition as a function of the reference value ($\beta_{MAP}$) of said parameter ($\beta$) relative to the same engine operating condition, and of past particulate accumulation in said particulate filter (9); and determining the amount of particulate ($m_S$) accumulated in said particulate filter (9) in the current engine operating condition as a function of the operating value ($\beta_{MOD}$) of said parameter ($\beta$) calculated for said current engine operating condition.

7. A method as claimed in claim 6 characterized in that each of said reference values ($\beta_{MAP}$) of said parameter ($\beta$) is determined at an initial calibration step by accumulating particulate in the particulate filter (9) for a given length of time in the steady engine operating condition associated with said reference value ($\beta_{MAP}$).

8. A method as claimed in claim 6, characterized in that said step of determining an operating value ($\beta_{MOD}$) of said parameter ($\beta$) relating to the current engine operating condition comprises the steps of:

comparing the reference value ($\beta_{MAP}$) of said parameter ($\beta$) relating to the current engine operating condition with a previous operating value ($\beta_{MOD\_OLD}$) of the parameter ($\beta$);

if the reference value ($\beta_{MAP}$) is less than or equal to said previous operating value ($\beta_{MOD\_OLD}$) making said operating value ($\beta_{MOD}$) equal to said reference value ($\beta_{MAP}$) in a time depending on engine operating conditions;

if said reference value ($\beta_{MAP}$) is greater than said previous operating value ($\beta_{MOD\_OLD}$), waiting until an amount of particulate greater than a predetermined amount (threshold) accumulates in said particulate filter (9), and calculating said operating value ($\beta_{MOD}$) as a function of said reference value ($\beta_{MAP}$) and said previous operating value ($\beta_{MOD\_OLD}$).

9. A method as claimed in claim 8, characterized in that said operating value ($\beta_{MOD}$) is calculated according to the following equation:

$$\beta_{MOD} = \beta_{MAP} - \frac{m_{S\_OLD}}{m_S} \cdot (\beta_{MAP} - \beta_{MOD\_OLD})$$

where:
- $\beta_{MOD}$ is said operating value of parameter $\beta$;
- $\beta_{MAP}$ is said reference value of parameter $\beta$;
- $\beta MOD_{OLD}$ is said previous operating value of parameter $\beta$;
- $m_S$ is the new amount of particulate accumulated; and
- $m_{S\_OLD}$ is the previously determined amount of particulate accumulated.

10. A method of determining the amount of partical ($m_S$) accumulated in a particulate filter (9), comprising the step of:

determining the at least one of the variation in spatial distribution of the particulate in said particulate filter (9) and the variation in the physical-chemical properties of the particulate as a function of the engine operating conditions and past particulate accumulation in said particulate filter (9);

evaluating the final corrected value $m_{S\_CORR}$ of particulate accumulated in a particulate filter (9), through the calculation of an offset $\Delta m$, to be added to the value of particulate accumulated in a particulate filter ($m_S$) estimated without considering at least one of the variation in spatial distribution of the particulate in said particulate filter (9) and the variation in the physical-chemical properties of the particulate due to partial regenerations (e.g. NOx-based spontaneous regeneration) and prolonged vehicle disuse ("parking" effect).

11. A method of determining the amount of particulate ($m_S$) accumulated in a particulate filter (9), comprising the steps of:

determining the at least one of the variation in spatial distribution of the particulate in said particulate filter (9) and the variation in the phyaical-chemical properties of the particulate as a function of the engine operating conditions and past particulate accumulation in said particulate filter (9);

determining an offset $\Delta m$ after a certain amount of time after key-on, according to the following equation:

$$\Delta m = m_{S\_CORR\_ECU} - m_S$$

where:
- $m_{S\_CORR\_ECU}$ is the value of $m_{S\_CORR}$ stored in the electronic control unit at the previous key-off;
- $m_S$ is the value of particulate accumulated in a particulate filter estimated without considering at least one of the variation in spatial distribution of the particulate in said particulate filter (9) and the variation in the physical-chemical properties of the particulate due to prolonged vehicle disuse ("parking" effect).

12. A method of determining the amount of particulate ($m_S$) accumulated in a particulate filter (9), comprising the step of:

determining the at least one of the variation in spatial distribution of the particulate in said particulate filter (9) and the variation in the phyaical-chemical properties of the particulate as a function of the engine operating conditions and past particulate accumulation in said particulate filter (9);

determining an offset $\Delta m$ after a partial regeneration (e.g. NOx-based spontaneous regeneration), according to the following equation:

$$\Delta m = m_{S\_CORR} - m_S$$

where:
- $m_{S\_CORR}$ is the value of particulate accumulated in a particulate filter before a partial regeneration (e.g. NOx-based spontaneous regeneration), decremented at every time step, during said partial regeneration state, with an experimentally estimated instantaneous value of particulate regenerated $m_{NOx}$ (a function of the engine operating conditions).
- $m_S$ is the value of particulate accumulated in a particulate filter estimated without considering at least one of the variation in spatial distribution of the particulate in said particulate filter (9) and the variation in the physical-chemical properties of the particulate due to partial regeneration (e.g. NOx-based spontaneous regeneration).

* * * * *